United States Patent [19]

Booth et al.

[11] 4,209,654

[45] Jun. 24, 1980

[54] RECYCLABLE BORON TRIFLUORIDE CATALYST AND METHOD OF USING SAME

[75] Inventors: Robert E. Booth; Francis E. Evans, both of Hamburg; Richard E. Eibeck, Orchard Park; Martin A. Robinson, East Amherst, all of N.Y.

[73] Assignee: Allied Chemical Corporation, Morris Township, N.J.

[21] Appl. No.: 951,911

[22] Filed: Oct. 16, 1978

[51] Int. Cl.$^2$ ............................ C07C 3/56; C07C 3/18
[52] U.S. Cl. ..................................... 585/465; 585/525
[58] Field of Search .......... 260/671 C, 671 P, 671 R; 585/465, 525, 644, 726

[56] References Cited

U.S. PATENT DOCUMENTS

| | | | |
|---|---|---|---|
| 2,425,839 | 8/1947 | Schulze et al. | 260/671 P |
| 2,836,634 | 5/1958 | Lee et al. | 260/671 P |
| 3,780,128 | 12/1973 | Shubkin | 585/525 |
| 3,855,342 | 12/1974 | Huang et al. | 585/726 |
| 4,032,591 | 6/1977 | Cupples et al. | 585/644 |

*Primary Examiner*—George Crasanakis
*Attorney, Agent, or Firm*—Alan M. Doernberg; Jay P. Friedenson

[57] ABSTRACT

When saturated with boron trifluoride, certain polyhydric alcohols form adducts which catalyze reactions for which boron trifluoride is catalytic. The adduct is recovered from the reaction mixture and recycled, greatly reducing boron and fluoride values in the product and in any effluent. Examples include propylation of toluene in the presence of a recycled adduct of boron trifluoride with mannitol or sorbitol.

12 Claims, No Drawings

RECYCLABLE BORON TRIFLUORIDE CATALYST AND METHOD OF USING SAME

BACKGROUND OF THE INVENTION

Boron trifluoride has found wide use as a catalyst for various reactions and has been proposed as a catalyst for additional reactions. Such reactions include hydrocarbon transfers (alkylations, cracking, isomerizations, polymerizations) and reactions involving functional groups (dehydration of alcohols, cyanation of olefins, conversion of aniline to diphenylamine, conversion of methylol to 4-methoxy-2-methyl-1-butene, reaction of ammonia and acrolein to form pyridine and reaction of sodium acetate and acetylene to form vinyl acetate). A drawback of the use of boron trifluoride is that it decomposes during reaction, preventing reuse and contributing boron and fluoride to either the product or an effluent stream, necessitating extra purification or recovery.

While attempts have been made to fix boron trifluoride to a polymer or inorganic support, these attempts have not produced a reusable boron trifluoride catalyst system practical for the wide variety of catalytic uses. For many particular reactions, a cocatalyst is provided with boron trifluoride to cause or enhance catalytic activity. Such cocatalysts have not, however, been used to retain the boron and fluoride values.

BRIEF DESCRIPTION OF THE INVENTION

It has been discovered that certain polyhydric alcohols form stable complexes or adducts with boron trifluoride which can catalyze reactions for which boron trifluoride is a catalyst and which can be separated from the reaction mixture with minimum loss of activity or boron and fluoride values.

Accordingly, the present invention includes an improvement in a method of reacting at least one unsaturated hydrocarbon in an alkyl transfer reaction of the type catalyzed by boron trifluoride. In the improvement, the reaction is conducted in the presence of a catalytic amount of a polyhydric alcohol saturated with boron trifluoride to form an adduct and the adduct is recovered from the product of the reaction and is recycled.

In one form of the invention the polyhydric alcohol is selected from the group consisting of linear compounds of the formula $CH_2OH-(CHOH)_n-CH_2OH$ where n is 1 to 5, pentaerythritol, crystalline cellulose and non-adjacent diols of 5-10 carbons of the formula $R_1-CHOH-CH_2-CHOH-R_2$ where $R_1$ and $R_2$ are each alkyl of 1-6 carbons.

In another form of the invention the reaction is conducted in the presence of a catalytic amount of an adduct formed by saturating with boron trifluoride a polyhydric alcohol selected from the group consisting of glycerine, tetritols, pentitols, hexitols, heptitols, pentaerythritol, crystalline polysaccharides, polyvinyl alcohol and non-adjacent diols of 4-10 carbons; the reaction is conducted at an elevated temperature at which the adduct is stirrable; the reaction mixture is cooled to a temperature at which the adduct becomes viscous; and the adduct is recovered from the reaction mixture and recycled.

The present invention also includes stable, recyclable catalyst adducts formed by the saturation with boron trifluoride of a polyhydric alcohol selected from the group consisting of glycerol, tetritols, pentitols, hexitols, heptitols, pentaerythritol, polyvinyl alcohol, crystalline polysaccharides and non-adjacent diols of 4–10 carbons.

DETAILED DESCRIPTION OF THE INVENTION

The stable catalyst adducts of the present invention are formed by saturation of polyhydric alcohols with $BF_3$. The product is referred to herein as an "adduct" without limitation as to its actual structure which, because of the observed ratio of one mole of $BF_3$ to two moles of hydroxyl in some cases, may be a chelate of the formula

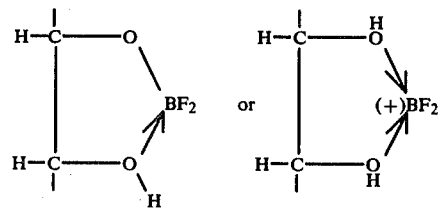

The polyhydric alcohols of the present invention include linear members of the formula $CH_2CH-(CHOH)_n-CH_2OH$ where n is 1 to 5, branched polyhydric alcohols having 3-6 hydroxyls such as pentaerythritol, polyvinyl alcohol and certain polysaccharides. The linear polyhydric alcohols include glycerin; the tetritols erythritol and threitol (D or L or racemic); the pentitols ribitol, xylitol and arabitol (D or L or racemic); the hexitols dulcitol, sorbitol, mannitol (D or L of racemic), iditol (D or L or racemic), talitol (D or L or racemic) and allitol; and the heptitols which include perseitol and sedoheptitol. Preferred are the hexitols and especially preferred are mannitol and sorbitol.

The polyhydric alcohols of the present invention also include diols with non-adjacent hydroxyls of 4–10 carbons such as 2,4-pentane diol. Preferred in this group are diols of the formula $R_1-CHOH-CH_2-CHOH-R_2$ where $R_1$ and $R_2$ are each alkyl of 1-6 carbons and together have 2-7 carbons.

Branched polyhydric alcohols having 3-6 hydroxyls are also suitable, and preferred in this group is pentaerythritol $C(CH_2OH)_4$.

Some, but not all sugars, both pentoses and hexoses, are suitable. Crystalline polysaccharides are also suitable, such as crystalline cellulose and some starches; while non-crystalline polysaccharides such as cellulose fiber and sucrose are generally unsuitable.

The first criterion for polyhydric alcohols suitable in the present invention is that they absorb $BF_3$ gas in substantial proportions. It appears that a minimum of about 0.3 moles $BF_3$ absorbed per mole of hydroxyls is required. Many but not all polyhydric alcohols tested which absorb such substantial quantities of $BF_3$ are active for one pass of alkylation or similar reaction. The second criterion for the polyhydric alcohol-$BF_3$ adduct is that it be separable from the product mixture of alkylation or similar reaction, either by distillation, decanting or some other technique, preferably by decanting based upon immiscibility or insolubility or solidification of the catalyst adduct on cooling. The third criterion is that the adduct be catalytically active for at least one additional pass of alkylation or similar reaction and preferably for at least four additional passes. Most preferred are adducts formed from polyhydric alcohols such as mannitol, sorbitol, glycerin, crystalline cellulose and pentaerythritol which give substantially constant activity on succeeding passes of alkylation.

The quantity of $BF_3$ absorbed varies, even among isomers such as mannitol (which absorbed about 3 moles $BF_3$) and sorbitol (which absorbed about 2 moles). Optical isomers such as D-mannitol and L-mannitol and mixtures thereof such as racemic mannitol would be expected to behave similarly. It is postulated that the stereochemical differences between, for example, sorbitol and mannitol cause one pair of adjacent hydroxyls to be good $BF_3$ acceptors in mannitol but poor $BF_3$ acceptors in sorbitol. The behavior of glycerin and xylitol in absorbing more $BF_3$ moles than the number of hydroxyl pairs suggests that the odd hydroxyl is also somewhat active. The resistence of the inositol used suggests a conformational arrangement which prevents $BF_3$ absorption, but does not necessarily indicate that other stereoisomers are inactive. The catechol adduct only lasted one run, at least for the cymeme reaction, because it failed to be easily separable from the alkylation product mixture in which it dissolved. Catechol and other polyhydric aromatics such as resorcinol are not, therefore, excluded provided that a suitable separation technique is used.

Of the polysaccharides tested, crystalline cellulose, starch and sucrose all gave absorption of at least about 0.3 moles $BF_3$ per mole and all three were active on the first pass. Sucrose and starch would be regarded, however, as unsuitable because of failure to retain activity after separation. Cellulose fiber failed to absorb $BF_3$ and could thus be rejected on the first criterion.

The reactions for which the present catalysts may be used are not limited to alkylations. Other hydrocarbon transfer reactions involving at least one unsaturated reactant, such as isomerizations, cracking and polymerizations for which boron trifluoride is catalytically active, may be conducted in the presence of the catalyst adducts. In addition, reactions involving functional groups such as cyanation of olefins, formation of pyridine and formation of vinyl acetate, may be practised with the catalyst adducts.

Reaction conditions may be similar to those used for the same reaction with boron trifluoride alone as catalyst. Because many of the catalyst adducts solidify at moderate temperatures, it is frequently desirable to maintain the reaction mixture at slightly elevated temperatures such as 40°–120° C. with agitation. Ceasing agitation, cooling or both frequently causes separation of catalyst adduct from the reaction mixture, enabling recovery and recycling by phase separation. With some reactions, it may be more convenient to distill the product from the reaction mixture, leaving the catalyst adduct for reaction with fresh reactant.

The ratio in each pass or in a continuous system at one time of catalyst adduct to reagent (monomer in the case of oligomerizations, the limiting reagent in the case of alkylations or other reactions between reagents) is not critical, but may be in the range of about 0.0001 to 10:1 with about 0.001 to 1:1 being preferred and about 0.005 to 0.1:1 being more preferred.

EXAMPLE 1

Propylation of Toluene with Mannitol-$BF_3$ Adduct $BF_3$ gas was passed into a stirred slurry of mannitol (50 g, 0.276 mole) and toluene (207 g) (dried of excess moisture by azeotropic distillation) at room temperature for seven hours. The adduct had separated as a gummy mass that could be agitated only at elevated temperatures. $BF_3$ addition was continued at 60°–70° for 16 hours, and 50°–60° for seven hours (viscosity had decreased somewhat). The mannitol absorbed 57.7 g $BF_3$, 0.851 mole, which is 3.1 moles $BF_3$ per mole of mannitol, and 0.51 mole $BF_3$ per hydroxyl group.

The toluene was decanted from the adduct (an immobile gum at room temperature) and fresh toluene (about 200 g) was stirred with adduct at about 60° with a $N_2$ purge to strip unreacted $BF_3$. When gas chromatography analysis of the toluene phase showed no $BF_3$, the toluene was again replaced, and propylene passed into the toluene-adduct mixture agitated at 62° for 3 hours. Gas chromatography analysis of the liquid phase showed it to contain 20.5% p-cymene. (The chromatogram has peaks that are probably attributable to o-cymene, and dipropyl-toluenes, but proof and quantitative determinations were not available for these.) The product mixture (200 g), decanted from the catalyst, was extracted twice with 200 ml water; analysis of the combined extracts showed the toluene-cymene product had 248 ppm boron and 590 ppm fluoride. The catalyst was washed by stirring at 60° with fresh toluene to remove cymenes.

Fresh toluene was added to the catalyst and stirred 2 hours at 60°; it now showed 0.8% p-cymene extracted from the catalyst. Propylene was passed in with agitation at 60°–80° for three hours. Analysis showed the toluene phase to be 44.5% p-cymene, or a gain of 43.7%. Water extraction and analysis showed that the toluene phase contained 87 ppm boron and 221 ppm fluoride.

In like manner the catalyst performed through two additional cycles. The conditions and results of all four cycles are displayed in Table 1.

Table 1

| Cycle | 1 | 2 | 3 | 4 |
|---|---|---|---|---|
| Propylation (hrs) | 5 | 3 | 3 | 3 |
| Temperature (°C.) | 62 | 60–80 | 65–86 | 60–63 |
| Initial p-cymene (vol. %) | 0 | 0.8 | 0.8 | 2.0 |
| Final p-cymene (vol. %) | 20.5 | 44.5 | 44 | 40 |
| Gain in p-cymene | 20.5 | 43.7 | 43.2 | 38 |
| Boron content of product (ppm) | 248 | 87 | — | 20 |
| Fluoride content of product (ppm) | 59 | 221 | 149 | 99 |

Other batches of mannitol-boron trifluoride adduct were used over ten and five cycles.

EXAMPLE 2

Propylation of Toluene With Sorbitol-$BF_3$ Adduct

In a procedure like that described in Example 1, $BF_3$ was added to sorbitol (50 g., 0.276 mole) at temperatures up to 85° (whatever temperature was required to preserve mobility through the gummy stages) over a 19 hour period. 40.7 g. $BF_3$ (0.600 mole) was absorbed, (equivalent to 2.17 moles per mole sorbitol or 0.36 per hydroxyl).

Propylation of toluene by this catalyst was conducted as detailed in Example 1, but, as shown below, the run time was shortened. In the first cycles, the p-cymene content had leveled off, but the toluene content was about 20%, and dipropyl toluenes showed prominently, indicating that cymeme was being propylated more than toluene.

Consequently, the third, fourth and fifth runs were shortened to two, one and one hour. The conditions and results are displayed in Table 2.

Table 2

| Cycle | 1 | 2 | 3 | 4 | 5 |
|---|---|---|---|---|---|
| Propylation (hours) | 3 | 3 | 2 | 1 | 1 |
| Temperature (°C.) | 77–94° | 91–98° | 70–86° | 80–83° | 75–81° |
| p-Cymene - initial % | 0.16 | 0.03 | 0.1 | 0.5 | 0.01 |
| p-Cymene - final % | 34 | 40 | 46.5 | 30.5 | 30 |
| p-Cymene- increase % | 33.8 | 40 | 46.5 | 30 | 30 |
| Boron - ppm | 268 | 99 | 214 | 7 | 187 |
| Fluoride - ppm | 511 | 244 | 471 | 28 | 472 |

EXAMPLE 3

Propylation of Toluene With Glycerin-BF$_3$ Adduct

Following the procedure of Example 1, BF$_3$ was added to glycerin. Though a liquid, the adduct formed a high-viscosity gum after about seven hours of adding BF$_3$ and required warming at 40°–50° for continued agitation. The BF$_3$ saturated product contained 1.93 moles BF$_3$ per mole of glycerin (0.64 per hydroxyl), and propylated toluene as shown in Table 3.

Table 3

| Cycle | 1 | 2 | 3 | 4 | 5 |
|---|---|---|---|---|---|
| Propylation (hours) | 3 | 3 | 3 | 3 | 3 |
| Temperature (°C.) | 54°–67° | 55°–67° | 56°–67° | 54°–72° | =°–68° |
| p-Cymene - initial % | <0.1 | 0.3 | 0.6 | 0.4 | 1.0 |
| p-Cymene - final % | 20.5 | 21.3 | 25.5 | 30.0 | 25.5 |
| p-Cymene - increase % | 20.5 | 21.0 | 24.9 | 29.6 | 24.5 |

EXAMPLE 4

Propylation of Toluene with Xylitol-BF$_3$ Adduct

Following the procedure of Example 1, BF$_3$ (26.0 g, 0.383 mole) was added to xylitol (25.3 g, 0.166 mole) at 40°–50°. The xylitol absorbed 2.30 moles BF$_3$ per mole, or 0.46 per hydroxyl, and propylated toluene as shown in Table 4.

Table 4

| Cycle | 1 | 2 | 3 |
|---|---|---|---|
| Time - hours | 3 | 3 | 3 |
| Temperature | 52–61° | 51–57° | 52–64° |
| p-Cymene - initial % | <0.01 | 0.25 | 1.1 |
| p-Cymene - final % | 22 | 15 | 8 |
| p-Cymene - increase % | 22 | 14.8 | 6.9 |

EXAMPLES 7, 11, 15 AND 18 AND COMPARATIVE EXAMPLES 5, 6, 8–10, 12–14 AND 16–17 AND 19 OTHER ADDUCTS

Following the procedure of Example 1, BF$_3$ addition of the other polyhydric alcohols shown in Table 5 was attempted, followed by propylation of toluene (except in Comparative Examples 10 and 16 where no BF$_3$ had been absorbed). Propylation temperatures were adjusted to control viscosity of the adduct and ranged from 40°–50° C. with less viscous adducts to 90°–105° with more viscous adducts. The results of these Examples and Comparative Examples, and the previous four Examples, are summarized in Table 5.

Table 5

| | | BF$_3$ Addition | | Propylation | |
|---|---|---|---|---|---|
| Example | Polyhydric Alcohol | BF$_3$ Mole/Mole | BF$_3$ Mole/OH | % p-Cymeme | No. of Cycles |
| 1 | Mannitol | 3.1 2.9 | 0.50 | 35–44% | 5 |
| 2 | Sorbitol | 2.2 2.1 | 0.36 | 35–40%[a] | 5 |
| 3 | Glycerin | 1.9 | 0.64 | 20–30% | 5 |
| 4 | Xylitol | 2.3 | 0.46 | 22,15,7[b] | 3 |
| C 5 | Starch | 2.4 | 0.79 | 13% | 1 |
| C 6 | Cellulose (fiber) | 0.2 | 0.07 | 1% | 1 |
| 7 | Cellulose (xtal) | 2.5 | 0.82 | 15–35% | 5 |
| C 8 | Sucrose | 2.7 | 0.34 | 3% | 1 |
| C 9 | Methyl Glucoside | 2.0 | 0.50 | 3% | 1 |
| C 10 | Inositol | 0 | 0 | — | — |
| 11 | Pentaerythritol | 1.8 | 0.45 | 13–18 | 5 |
| C 12 | Dipentaerythritol | 3.0 | 0.50 | 1% | 1 |
| C 13 | Catechol | 1.0 | 0.50 | 12%[e] | 1 |
| C 14 | Ascorbic Acid | [c] | | 3% | 1 |
| 15 | Polyvinyl Alcohol | [d] | | 6% | 2 |
| C 16 | Oxalic Acid | 0 | 0 | — | — |
| C 17 | Triethanolamine | [c] | — | 7% | 1 |
| 18 | 2,4-Pentanediol | 2.1 | 1.07 | 45–56% | 3 |
| 19 | Poly(hydroxy-methylene)[e] | 0 | 0 | — | — |

[a]With Sorbitol-BF$_3$, the % p-cymene was about constant in 3-hr. runs, but toluene was nearly exhausted and poly-propyltoluenes very much in evidence. One-hour runs produced 30% p-cymene.
[b]The percentages decreased as shown over three cycles, indicating the adduct was decomposing and was not completely recyclable.
[c]Ratio not determined but apparently in excess of 1.
[d]The catechol-BF$_3$ adduct was not recyclable here — it totally dissolved in the toluene-cymene mixture (though not originally soluble in toluene alone).
[e]A polymer of the formula H—(CHOH)$_n$—H formed by the homopolymerization of vinylidene carbonate and hydrolysis of the product.

It should be appreciated that cellulose fiber (C6), inositol (C10), oxalic acid (C16) and poly(hydroxymethylene) (C19) are unsuitable polyhydric alcohols by virtue of the inability to meet the first criteria by absorbing BF$_6$. Starch (C5), sucrose (C8), methyl glucoside (C9), dipentaerythritol (C12), ascorbic acid (C14) and triethanolamine (C17) fail either the second criteria of catalytic activity or the third criteria of recyclability. Catechol (C13) also fails the third criteria, but might be suitable in other BF$_3$ catalyzed reactions, especially those not involving aromatics. Polyvinyl alcohol (15) is regarded as suitable, but not preferred, because of its limited recyclability. Xylitol (4) is also less preferred because of apparent degradation on recycling. Of the additional adducts tested, only those formed from pentaerythritol (11) and crystalline cellulose (7) retained activity on recycling, but at a level lower than 2,4-pentanediol and the preferred hexitols: mannitol and sorbitol.

EXAMPLE 20

Polymerization of Diisobutylene With Mannitol-BF$_3$ Adduct

Mannitol.BF$_3$ catalyst was prepared by the addition of BF$_3$ (35.8 g, 0.528 mole) to mannitol (31.2 g, 0.171 mole) in toluene over a 24 hour period at 50°–60°. The adduct contained 3.08 moles BF$_3$ per mole mannitol, or 0.51 mole per hydroxyl. All toluene was decanted from the catalyst. Dropwise addition of diisobutylene was begun at room temperature (about 7 ml/min.). An exothermic reaction heated the mixture to 62° in 15 minutes. After holding at 62° for 20 additional minutes, external heating was applied. Diisobutylene (213 ml, 152 grams) was added in 35 minutes, and the reaction mixture was held at 53°–62° for an additional 4½ hours. The decanted liquid phase had a Brookfield viscosity of 11.0 centipoise (diisobutylene-1.0 cps). Distillation of the liquid phase delivered about 30 g. at 180°–190° (this must be the dimer: tetraisobutylene; diisobutylene boils at 101°–102° C.). The clear, yellow, oily residue has a Brookfield viscosity of 10.0 cps.

As a control for the above experiment, diisobutylene was polymerized by the diethyl ether complex of BF$_3$. To 162 g. diisobutylene stirring at room temperature in a flask, BF$_3$-diethyl ether complex (27.7 g) was added dropwise over a 10 minute period. An exotherm peaked at 61° in 7 minutes, then external heating was applied to hold the mixture at 60°–70° for 6½ hours. At room temperature the mixture separated into two layers: the lower layer (about 24 g) proved to be mainly ether; the upper layer (about 165 g) was washed five times with water to decompose and remove spent BF$_3$, dried over CaCl$_2$ and distilled. A few drops collected at 30°–40° (ether), then nothing until 25 g was collected at 180°–190°. The clear, yellow, oily residue has a Brookfield viscosity of 21.0 cps.

It will be appreciated that the control produced lower yields of tetraisobutylene (comparable in physical properties) with an etherate complex that merely fixes the BF$_3$ before reaction in a convenient form for handling, and does not fix the BF$_3$ for recovery and recycling.

EXAMPLE 21

Polymerization of 1-Decene With Mannitol-BF$_3$ Adduct

Mannitol.BF$_3$ catalyst was prepared by the addition of BF$_3$ (53.7 grams, 0.792 mole) to mannitol (50 grams, 0.274 mole) in toluene over a 23 hour period at 60°–70° C. The adduct contained 2.89 moles BF$_3$ per mole of mannitol, or 0.48 mole per hydroxyl. All toluene was decanted from the catalyst and the catalyst was washed with 1-decene to remove the last traces of toluene.

1-Decene (200 mole, 148.2 gram) was agitated with the mannitol.BF$_3$ adduct for 12 hours at 50°–60° C. A chromatogram of a sample of the liquor showed oligomers and great depletion of the decene. The liquor was decanted, washed with concentrated HCl, water, aqueous Na$_2$CO$_3$, four more times with water, dried and distilled (124.2 grams). Fractionation developed three samples (1-Decene boils 172° C.):

| Fr. 1 | b. 144–160° | 12.7 grams | 10.2% |
| Fr. 2 | b. 160–210° | 7.7 grams | 6.2% |
| Fr. 3 | Residue | 103.8 grams | 83.6% |

A chromatogram showed approximately 0.1% low-boilers in Fraction 3, the remainder being oligomers of 1-decene, so a yield of about 84% oligomers is assumed.

This batch of mannitol.BF$_3$ was cycled for three more oligomerizations of 1-decene in about the same manner. Results of all four cycles are tabulated below:

| Cycle | Temp | Time | Oligomer Yield |
|---|---|---|---|
| I | 50–60° | 12 hr. | 84% |
| II | 55–70° | 4 hr. | 92% |
| III | 50–70° | 7 hr. | 94% |
| IV | 50–55° | 8 hr. | 95% |

We claim:

1. In a method of reacting at least one unsaturated hydrocarbon in an alkyl transfer reaction of the type catalyzed by boron trifluoride, the improvement which comprises conducting the reaction in the presence of a catalytic amount of an adduct formed by saturating with boron trifluoride a polyhydric alcohol selected from the group consisting of linear compounds of the formula CH$_2$OH—(CHOH)$_n$—CH$_2$OH where n is 1 to 5, pentaerythritol, crystalline cellulose and non-adjacent diols of 5–10 carbons of the formula R$_1$—CHOH—CH$_2$—CHOH—R$_2$ where R$_1$ and R$_2$ are each alkyl of 1–6 carbons, recovering the adduct from the reaction mixture and recycling the adduct.

2. The method of claim 1 wherein the polyhydric alcohol is a linear compound of the formula CH$_2$OH—(CHOH)$_4$—CH$_2$OH.

3. The method of claim 2 wherein the polyhydric alcohol is mannitol.

4. The method of claim 2 wherein the polyhydric alcohol is sorbitol.

5. The method of claim 1 wherein the polyhydric alcohol is crystalline cellulose.

6. The method of claim 1 wherein the polyhydric alcohol is a non-adjacent diol of 5–10 carbons of the formula R$_1$—CHOH—CH$_2$—CHOH—R$_2$ where R$_1$ and R$_2$ are each alkyl of 1–6 carbons.

7. The method of claim 6 wherein the polyhydric alcohol is 2,4-pentanediol.

8. The method of claim 1 wherein said reaction is the alkylation with an olefinic hydrocarbon of 2–5 carbons of an aromatic hydrocarbon of 6–10 carbons.

9. The method of claim 8 wherein said olefinic hydrocarbon is propylene.

10. The method of claim 1 wherein the adduct contains at least about 0.3 mole of BF$_3$ per mole of hydroxyl 11. In a method of reacting at least one unsaturated hydrocarbon in an alkyl transfer reaction of the type catalyzed by boron trifluoride, the improvement which comprises conducting the reaction in the presence of a catalytic amount of an adduct formed by saturating with boron trifluoride a polyhydric alcohol selected from the group consisting of glycerine, tetritols, pentitols, hexitols, heptitols, pentaerythritol, crystalline polysaccharides, polyvinyl alcohol and non-adjacent diols of 4–10 carbons, conducting the reaction at an elevated temperature at which the adduct is stirrable, cooling the reaction mixture to a temperature at which the adduct becomes viscous, recovering the adduct from the reaction mixture and recycling the adduct.

12. The method of claim 1, claim 2, claim 3, claim 4, claim 5, claim 6, claim 7, claim 8, claim 9, or claim 11 wherein said adduct is the product of at least about 0.3 moles $BF_3$ per mole of hydroxyl of said polyhydric alcohol and wherein said adduct is catalytically active for at least four additional passes to said alkyl transfer reaction.

* * * * *